United States Patent
Stein

(10) Patent No.: US 8,324,975 B2
(45) Date of Patent: *Dec. 4, 2012

(54) PROPAGATION TUNED OSCILLATOR FOR ORTHOPEDIC PARAMETER MEASUREMENT

(76) Inventor: Marc Stein, Chandler, AZ (US)

( * ) Notice: Subject to any disclaimer, the term of this patent is extended or adjusted under 35 U.S.C. 154(b) by 161 days.

This patent is subject to a terminal disclaimer.

(21) Appl. No.: 12/825,913

(22) Filed: Jun. 29, 2010

(65) Prior Publication Data

US 2010/0331718 A1  Dec. 30, 2010

Related U.S. Application Data

(60) Provisional application No. 61/221,894, filed on Jun. 30, 2009.

(51) Int. Cl.
*G01R 27/04* (2006.01)
*A61B 5/103* (2006.01)

(52) U.S. Cl. .......... 331/96; 331/187; 324/636; 324/639; 324/644; 600/587; 606/53

(58) Field of Classification Search ................. 331/1 R, 331/96, 154, 187; 324/629, 633, 636, 637, 324/639, 642, 644, 647; 600/587, 595; 606/53, 606/60, 87, 88, 102; 623/20.14
See application file for complete search history.

(56) References Cited

U.S. PATENT DOCUMENTS

| | | | |
|---|---|---|---|
| 4,271,371 A * | 6/1981 | Furuichi et al. ......... 310/316.01 |
| 4,277,758 A * | 7/1981 | Mishiro ......... 331/1 R |
| 5,197,488 A | 3/1993 | Kovacevic | |
| 5,470,354 A | 11/1995 | Hershberger et al. | |
| 5,491,604 A * | 2/1996 | Nguyen et al. ......... 361/278 |
| 5,683,396 A | 11/1997 | Tokish et al. | |
| 5,688,279 A | 11/1997 | McNulty et al. | |
| 5,871,018 A | 2/1999 | Delp et al. | |
| 6,171,252 B1 | 1/2001 | Roberts | |
| 6,245,109 B1 | 6/2001 | Mendes et al. | |
| 6,583,630 B2 | 6/2003 | Mendes et al. | |
| 6,621,278 B2 | 9/2003 | Ariav | |
| 6,701,174 B1 | 3/2004 | Krause et al. | |
| 6,714,763 B2 | 3/2004 | Hamel et al. | |
| 6,821,299 B2 | 11/2004 | Kirking et al. | |
| 6,856,141 B2 | 2/2005 | Ariav | |
| 7,001,346 B2 | 2/2006 | White | |
| 7,097,662 B2 | 8/2006 | Evans et al. | |
| 7,190,237 B2 * | 3/2007 | Zivanovic et al. ............ 331/155 |
| 7,195,645 B2 | 3/2007 | Disilvestro et al. | |
| 7,256,695 B2 | 8/2007 | Hamel et al. | |
| 7,295,724 B2 | 11/2007 | Wang et al. | |
| 7,378,916 B2 * | 5/2008 | Oita et al. ......... 331/158 |
| 7,382,205 B2 * | 6/2008 | Van Beek ......... 331/154 |
| 7,442,196 B2 | 10/2008 | Fisher et al. | |

(Continued)

*Primary Examiner* — Levi Gannon

(57) ABSTRACT

A measurement system for capturing a transit time, phase, or frequency of energy waves propagating through a propagation medium (702) is disclosed. The measurement system comprises two different closed-loop feedback paths. The first path includes a transducer driver (726), a transducer (704), a propagation structure (702), a transducer (706), and a zero-crossing receiver (740). The series and parallel resonance of the transducer (704) does not overlap the series and parallel resonance of the transducer (706). A second path includes a transducer driver (1126), a transducer (1104), a propagation medium (1102), a reflecting surface (1106), and an edge-detect receiver (1140). Each positive closed-loop path maintains the emission, propagation, and detection of energy waves in the propagation medium (702, 1102). In either path, a propagation tuned oscillator maintains positive closed-loop feedback of the system that sustains detection, emission, and propagation of energy waves or pulses in a medium.

18 Claims, 9 Drawing Sheets

U.S. PATENT DOCUMENTS

| | | |
|---|---|---|
| 7,482,732 B2 * | 1/2009 | Kalantar-Zadeh ....... 310/323.21 |
| 7,575,602 B2 | 8/2009 | Amirouche et al. |
| 7,578,821 B2 | 8/2009 | Fisher et al. |
| 7,587,945 B2 | 9/2009 | Crottet et al. |
| 7,615,055 B2 | 11/2009 | DiSilvestro |
| 7,632,283 B2 | 12/2009 | Heldreth |
| 8,111,108 B2 * | 2/2012 | Gaidarzhy et al. ............ 331/154 |
| 2002/0029784 A1 | 3/2002 | Stark et al. |
| 2005/0020941 A1 | 1/2005 | Tarabichi |
| 2006/0058798 A1 | 3/2006 | Roman et al. |
| 2006/0232408 A1 | 10/2006 | Nycz et al. |
| 2006/0271112 A1 | 11/2006 | Martinson et al. |
| 2007/0219561 A1 | 9/2007 | Lavallee et al. |
| 2007/0272747 A1 | 11/2007 | Woods et al. |

\* cited by examiner

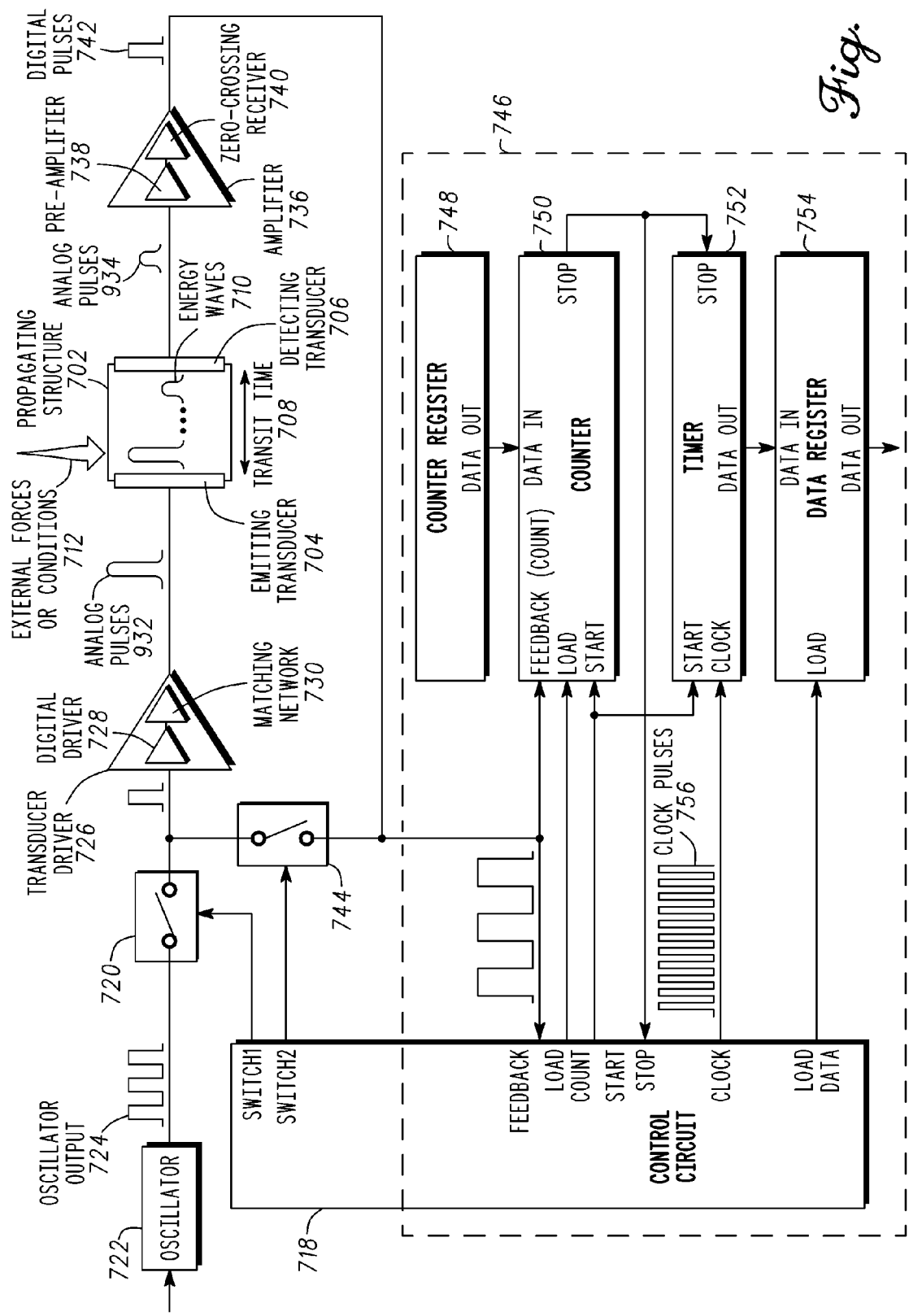

PROPAGATION TUNED OSCILLATOR FOR ORTHOPEDIC PARAMETER MEASUREMENT

CROSS-REFERENCE TO RELATED APPLICATIONS

This application claims the priority benefit of U.S. provisional patent applications No. 61/221,761, 61/221,767, 61/221,779, 61/221,788, 61/221,793, 61/221,801, 61/221,808, 61/221,817, 61/221,867, 61/221,874, 61/221,879, 61/221,881, 61/221,886, 61/221,889, 61/221,894, 61/221,901, 61/221,909, 61/221,916, 61/221,923, and 61/221,929 all filed 30 Jun. 2009; the disclosures of which are hereby incorporated herein by reference in their entirety.

FIELD

The present invention pertains generally to measurement of physical parameters, and particularly to, but not exclusively, to real-time measurement of changes in the transit time of energy waves or pulses propagating within energy propagating structures or media.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved as information from simulations, mechanical prototypes, and long-term patient joint replacement data is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 9 is an exemplary block diagram of a propagation tuned oscillator (PTO) for operation in pulse mode;

DETAILED DESCRIPTION

Figure 1:
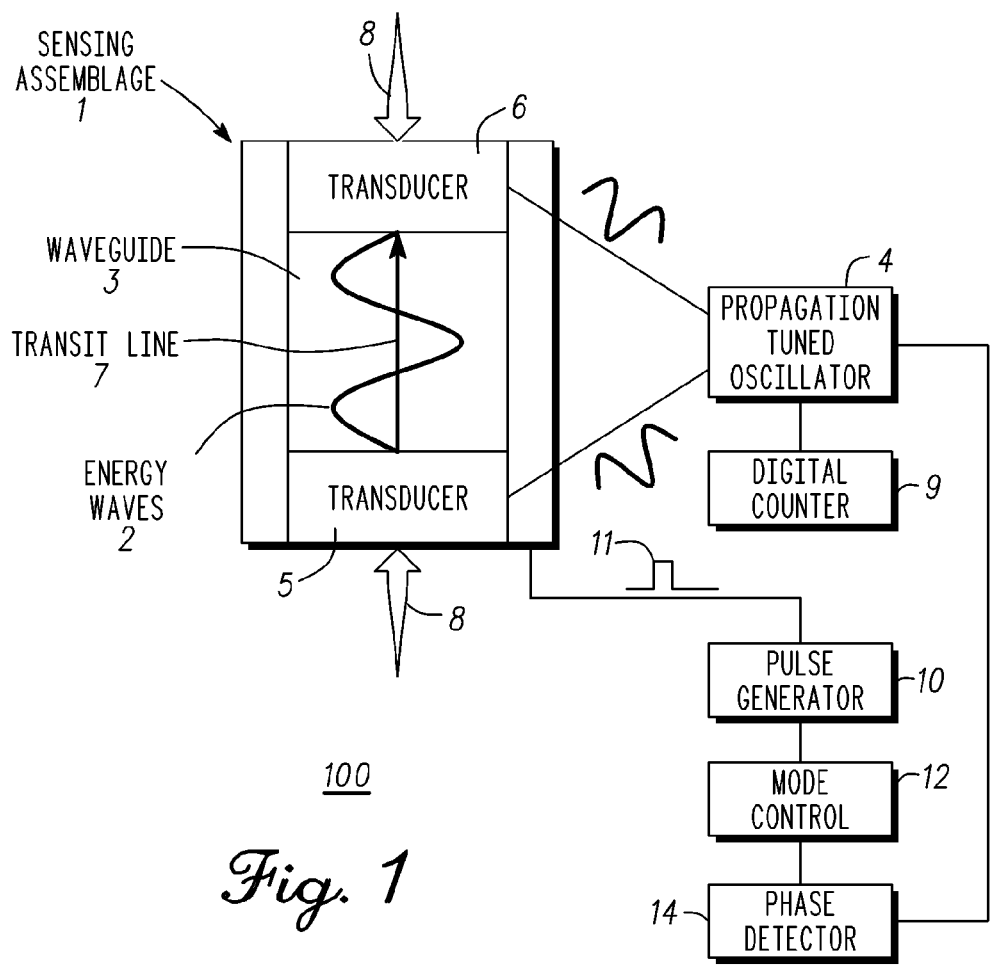
FIG. 1 is an exemplary block diagram of a propagation tuned oscillator (PTO) to maintain positive closed-loop feedback in accordance with an exemplary embodiment.

Embodiments of the invention are broadly directed to measurement of physical parameters, and more particularly, to real-time measurement of load, force, pressure, displacement, density, viscosity, or localized temperature by changes in the transit time of energy waves or pulses propagating within energy propagating structures or media.

In a first embodiment, a propagation tuned oscillator (PTO) is provided to maintain positive closed-loop feedback of energy waves in one or more energy propagating structures of a sensing assembly. The energy waves propagate through a medium in an energy propagating structure. A positive feedback closed-loop circuit causes the oscillator to tune the resonant frequency of the energy waves in accordance with physical changes in the one or more energy propagating structures; hence the term, propagation tuned oscillator. Detection of a propagated energy wave through at least a portion of the medium is detected by the PTO. The detection of the propagated energy wave initiates an energy wave emission into the medium thereby sustaining a process by which energy waves continually propagate through the medium.

In general, the PTO is used to measure a parameter. The parameter is applied to the medium of the energy propagating structure. The parameter causes a physical change in the medium. In one embodiment, the physical change is a dimensional change such as a change in length resulting from externally applied forces or pressure. The physical changes in the energy propagating structures change in direct proportion to the external applied forces and can be precisely evaluated to measure the applied forces.

The medium of the energy propagating structure is incorporated into a unity gain closed loop circuit to create the PTO. Movement or physical changes in the propagation properties of the medium alter the resonant frequency of the oscillator thus changing the oscillation frequency of the closed loop circuit. The PTO in conjunction with the energy propagating structure can be used to measure parameters of the muscular-skeletal system. In a non-limiting example, the energy propagating structure is placed within or coupled to a natural or artificial joint of the muscular-skeletal system to measure joint loading. The positive closed-loop feedback allows continuous emission and measurement of propagated energy waves over a predetermined period of time. In one embodiment, the PTO maintains an integer number of energy waves in the medium when in positive closed-loop feedback. A transit time, frequency, or phase of propagated energy waves are measured. The material properties of the medium in which the energy waves propagate have a known relationship to force. In the example, the length of the medium changes with the force applied thereon. The transit time, frequency, or phase translates directly to the length traversed by the energy wave, which can then be converted to a force measurement by way of the material (e.g.) length to force relationship. Changes in frequency of the PTO are digitized to evaluate the intensity, level, and direction of externally applied forces or pressure of the example parameter measurement. The reported measurements are instrumental in a wide range of applications including, but not limited to, frequency compensation; control of, or alarms for, physical systems; or monitoring or measuring physical parameters of interest.

In one configuration, the PTO employs a continuous mode (CM) of operation to tune a resonant frequency of transmitted energy waves by way of positive feedback closed-loop circuit to determine levels of applied forces on the waveguide.

In another configuration, the PTO employs a pulse mode (PM) of operation to tune a resonant frequency of transmitted pulses by way of positive feedback closed-loop circuit to determine levels of applied forces on the waveguide.

In a second embodiment, a wireless sensing module comprises the PTO, one or more sensing assemblies, one or more load surfaces, an accelerometer, electronic circuitry, a transceiver, and an energy supply. The wireless sensing module measures forces and transmits the measurement data to a secondary system for further processing and display. The electronic circuitry in conjunction with the sensing assemblies accurately measures physical displacements of the load surfaces on the order of a few microns along various physical dimensions. The sensing assembly physically changes in response to an applied force, such as an applied load. Electronic circuitry operating in a positive feedback closed-loop circuit configuration with the PTO precisely measures changes in propagation time due to changes in the length of the waveguides; physical length changes which occur in direct proportion to the applied force.

FIG. 1 is an exemplary block diagram 100 of a propagation tuned oscillator (PTO) 4 to maintain positive closed-loop feedback in accordance with an exemplary embodiment. The measurement system includes a sensing assemblage 1 and propagation tuned oscillator (PTO) 4 that detects energy waves 2 in one or more waveguides 5 of the sensing assemblage 1. In one embodiment, energy waves 2 are ultrasound waves. A pulse 11 is generated in response to the detection of energy waves 2 to initiate a propagation of a new energy wave in waveguide 3.

The sensing assemblage 1 comprises transducer 5, transducer 6, and a waveguide 3 (or energy propagating structure). In a non-limiting example, sensing assemblage 1 is affixed to load bearing or contacting surfaces 8. External forces applied to the contacting surfaces 8 compress the waveguide 3 and change the length of the waveguide 3. Under compression, transducers 5 and 6 will move closer together. The change in distance affects the transit time 7 of energy waves 2 transmitted and received between transducers 5 and 6. The propagation tuned oscillator 4 in response to these physical changes will detect each energy wave sooner (e.g. shorter transit time) and initiate the propagation of new energy waves associated with the shorter transit time. As will be explained below, this is accomplished by way of PTO 4 in conjunction with the pulse generator 10, the mode control 12, and the phase detector 14.

Notably, changes in the waveguide 3 (energy propagating structure or structures) alter the propagation properties of the medium of propagation (e.g. transit time 7). The energy wave can be a continuous wave or a pulsed energy wave. A pulsed energy wave approach reduces power dissipation allowing for a temporary power source such as a battery or capacitor to power the system during the course of operation. In at least one exemplary embodiment, transducer 5 provides to a first surface of waveguide 3 a continuous wave energy wave or a pulsed energy wave. The continuous wave or pulsed energy wave propagates into waveguide 3. In a non-limiting example, transducer 5 is a piezo-electric device capable of transmitting and receiving acoustic signals in the ultrasonic frequency range.

Transducer 6 is coupled to a second surface of waveguide 3 to receive the propagated pulsed signal and generates a corresponding electrical signal. The electrical signal output by transducer 6 is coupled to phase detector 14. In general, phase detector 14 compares the timing of a selected point on the waveform of the detected energy wave with respect to the timing of the same point on the waveform of other propagated energy waves. In a first embodiment, phase detector 14 can be a zero-crossing receiver. In a second embodiment, phase detector 14 can be an edge-detect receiver. In the example where sensing assemblage 1 is compressed, the detection of the propagated energy waves 2 occurs earlier (due to the length/distance reduction of waveguide 3) than a signal prior to external forces being applied to contacting surfaces. Pulse generator 10 generates a new pulse in response to detection of the propagated energy waves 2 by phase detector 14. The new pulse is provided to transducer 5 to initiate a new energy wave sequence. Thus, each energy wave sequence is an individual event of energy wave propagation, energy wave detection, and energy wave emission that maintains energy waves 2 propagating in waveguide 3.

The transit time 7 of a propagated energy wave is the time it takes an energy wave to propagate from the first surface of waveguide 3 to the second surface. There is delay associated with each circuit described above. Typically, the total delay of the circuitry is significantly less than the propagation time of an energy wave through waveguide 3. In addition, under equilibrium conditions variations in circuit delay are minimal. Multiple pulse to pulse timings can be used to generate an average time period when change in external forces occur relatively slowly in relation to the pulsed signal propagation time such as in a physiologic or mechanical system. The digital counter 9 in conjunction with electronic components counts the number of propagated energy waves to determine a corresponding change in the length of the waveguide 3. These changes in length change in direct proportion to the external force thus enabling the conversion of changes in parameter or parameters of interest into electrical signals.

In at least one exemplary embodiment, propagation tuned oscillator 4 in conjunction with one or more sensing assemblages 1 are used to take measurements on a muscular-skeletal system. In a non-limiting example, sensing assemblage 1 is placed between a femoral prosthetic component and tibial prosthetic component to provide measured load information that aids in the installation of an artificial knee joint. Sensing assemblage 1 can also be a permanent component or a muscular-skeletal joint or artificial muscular-skeletal joint to monitor joint function. The measurements can be made in extension and in flexion. In the example, assemblage 1 is used to measure the condyle loading to determine if it falls within a predetermined range and location. Based on the measurement, the surgeon can select the thickness of the insert such that the measured loading and incidence with the final insert in place will fall within the predetermined range. Soft tissue tensioning can be used by a surgeon to further optimize the force or pressure. Similarly, two assemblages 1 can be used to measure both condyles simultaneously or multiplexed. The difference in loading (e.g. balance) between condyles can be measured. Soft tissue tensioning can be used to reduce the force on the condyle having the higher measured loading to reduce the measured pressure difference between condyles.

One method of operation holds the number of energy waves propagating through waveguide 3 as a constant integer number. A time period of an energy wave corresponds to energy wave periodicity. A stable time period is one in which the time period changes very little over a number of energy waves. This occurs when conditions that affect sensing assemblage 1 stay consistent or constant. Holding the number of energy waves propagating through waveguide 3 to an integer number is a constraint that forces a change in the time between pulses when the length of waveguide 3 changes. The resulting change in time period of each energy wave corresponds to a change in aggregate energy wave time period that is captured using digital counter 9 as a measurement of changes in external forces or conditions applied to contacting surfaces 8.

A further method of operation according to one embodiment is described hereinbelow for energy waves 2 propagating from transducer 5 and received by transducer 6. In at least one exemplary embodiment, energy waves 2 is an ultrasonic energy wave. Transducers 5 and 6 are piezo-electric resonator transducers. Although not described, wave propagation can occur in the opposite direction being initiated by transducer 6 and received by transducer 5. Furthermore, detecting ultrasound resonator transducer 6 can be a separate ultrasound resonator as shown or transducer 5 can be used solely depending on the selected mode of propagation (e.g. reflective sensing). Changes in external forces or conditions applied to contacting surfaces 8 affect the propagation characteristics of waveguide 3 and alter transit time 7. As mentioned previously, propagation tuned oscillator 4 holds constant an integer number of energy waves 2 propagating through waveguide 3 (e.g. an integer number of pulsed energy wave time periods) thereby controlling the repetition rate. As noted above, once PTO 4 stabilizes, the digital counter 9 digitizes the repetition rate of pulsed energy waves, for example, by way of edge-detection, as will be explained hereinbelow in more detail.

In an alternate embodiment, the repetition rate of pulsed energy waves 2 emitted by transducer 5 can be controlled by pulse generator 10. The operation remains similar where the parameter to be measured corresponds to the measurement of the transit time 7 of pulsed energy waves 2 within waveguide 3. It should be noted that an individual ultrasonic pulse can comprise one or more energy waves with a damping wave shape. The energy wave shape is determined by the electrical and mechanical parameters of pulse generator 10, interface material or materials, where required, and ultrasound resonator or transducer 5. The frequency of the energy waves within individual pulses is determined by the response of the emitting ultrasound resonator 4 to excitation by an electrical pulse 11. The mode of the propagation of the pulsed energy waves 2 through waveguide 3 is controlled by mode control circuitry 12 (e.g., reflectance or uni-directional). The detecting ultrasound resonator or transducer may either be a separate ultrasound resonator or transducer 6 or the emitting resonator or transducer 5 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound energy waves within a waveguide of known length can be achieved by modulating the repetition rate of the ultrasound energy waves as a function of changes in distance or velocity through the medium of propagation, or a combination of changes in distance and velocity, caused by changes in the parameter or parameters of interest.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light. Furthermore, the velocity of ultrasound waves within a medium may be higher than in air. With the present dimensions of the initial embodiment of a propagation tuned oscillator the waveguide is approximately three wavelengths long at the frequency of operation.

Measurement by propagation tuned oscillator 4 and sensing assemblage 1 enables high sensitivity and signal-to-noise ratio as the time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Figure 2:
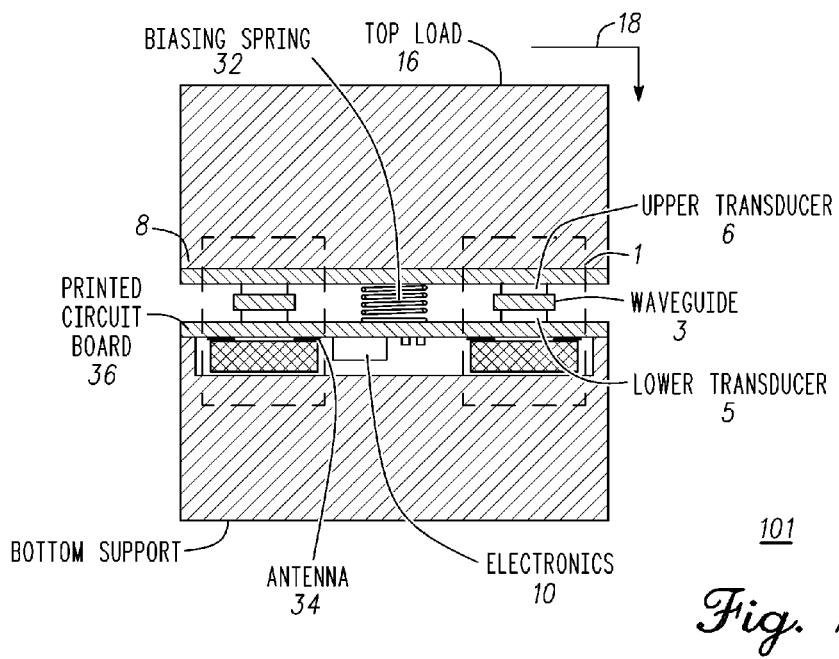
FIG. 2 is a simplified cross-sectional view of a sensing module in accordance with an exemplary embodiment.

FIG. 2 is a simplified cross-sectional view of a sensing module 101 in accordance with an exemplary embodiment. The sensing module (or assemblage) is an electro-mechanical assembly comprising electrical components and mechanical components that when configured and operated in accordance with a sensing mode performs as a positive feedback closed-loop measurement system. The measurement system can precisely measure applied forces, such as loading, on the electro-mechanical assembly.

In one embodiment, the electrical components can include ultrasound resonators or transducers, ultrasound waveguides, and signal processing electronics, but are not limited to these. The mechanical components can include biasing springs 32, spring retainers and posts, and load platforms 16, but are not limited to these. The electrical components and mechanical components can be inter-assembled (or integrated) onto a printed circuit board 36 to operate as a coherent ultrasonic measurement system within sensing module 101 and according to the sensing mode. As will be explained hereinbelow in more detail, the signal processing electronics incorporate edge detect circuitry that detects an edge of a signal after it has propagated through waveguide 3. The detection initiates the generation of a new energy wave by an ultrasound resonator or transducer that is coupled to waveguide 3 for propagation therethrough. A change in transit time of an energy wave through waveguide 3 is measured and correlates to a change in material property of waveguide 3.

Sensing module 101 comprises one or more assemblages 1 each comprised one or more ultrasound resonators. As illustrated, waveguide 3 is coupled between transducers 5 and 6 and affixed to load bearing or contacting surfaces 8. In one exemplary embodiment, an ultrasound signal is coupled for propagation through waveguide 3. The sensing module 101 is placed, attached to, or affixed to, or within a body, instrument, or other physical system 18 having a member or members 16 in contact with the load bearing or contacting surfaces 8 of the sensing module 101. This arrangement facilitates translating the parameters of interest into changes in the length or compression or extension of the waveguide or waveguides 3 within the sensing module 101 and converting these changes in length into electrical signals. This facilitates capturing data, measuring parameters of interest and digitizing that data, and then subsequently communicating that data through antenna 34 to external equipment with minimal disturbance to the operation of the body, instrument, appliance, vehicle, equipment, or physical system 18 for a wide range of applications.

The sensing module 101 supports three modes of operation of energy wave propagation and measurement: reflectance, unidirectional, and bi-directional. These modes can be used as appropriate for each individual application. In unidirectional and bi-directional modes, a chosen ultrasound resonator or transducer is controlled to emit pulses of ultrasound waves into the ultrasound waveguide and one or more other ultrasound resonators or transducers are controlled to detect the propagation of the pulses of ultrasound waves at a specified location or locations within the ultrasound waveguide. In reflectance or pulse-echo mode, a single ultrasound or transducer emits pulses of ultrasound waves into waveguide 3 and subsequently detects pulses of echo waves after reflection from a selected feature or termination of the waveguide. In pulse-echo mode, echoes of the pulses can be detected by controlling the actions of the emitting ultrasound resonator or transducer to alternate between emitting and detecting modes of operation. Pulse and pulse-echo modes of operation may require operation with more than one pulsed energy wave propagating within the waveguide at equilibrium.

Many parameters of interest within physical systems or bodies can be measured by evaluating changes in the transit time of energy pulses. The frequency, as defined by the reciprocal of the average period of a continuous or discontinuous signal, and type of the energy pulse is determined by factors such as distance of measurement, medium in which the signal travels, accuracy required by the measurement, precision required by the measurement, form factor, power constraints, and cost. In the non-limiting example, pulses of ultrasound energy provide accurate markers for measuring transit time of the pulses within waveguide 3. In general, an ultrasonic signal is an acoustic signal having a frequency above the human hearing range (e.g. >20 KHz) including frequencies well into the megahertz range. In one embodiment, a change in transit time of an ultrasonic energy pulse corresponds to a difference in the physical dimension of the waveguide from a previous state. For example, a force or pressure applied across the knee joint compresses waveguide 3 to a new length and changes the transit time of the energy pulse When integrated as a sensing module and inserted or coupled to a physical system or body, these changes are directly correlated to the physical changes on the system or body and can be readily measured as a pressure or a force.

Figure 3:
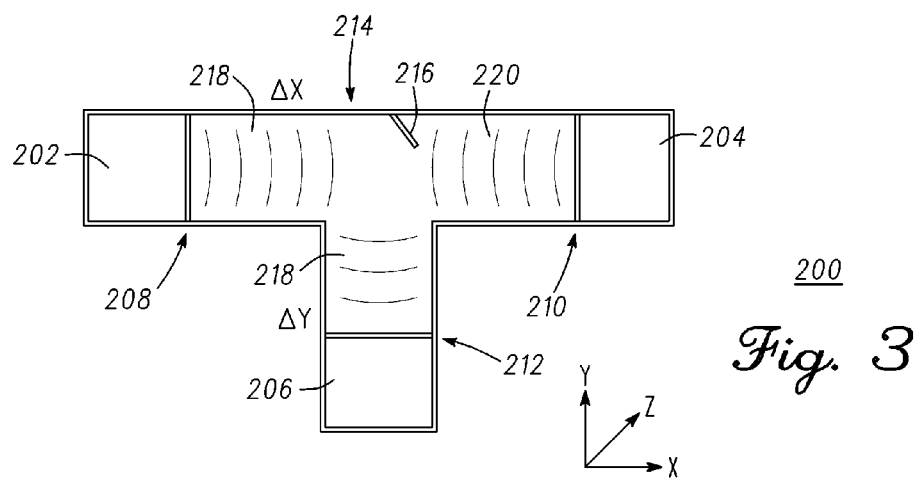
FIG. 3 is an exemplary assemblage for illustrating reflectance and unidirectional modes of operation in accordance with an exemplary embodiment.

FIG. 3 is an exemplary assemblage 200 for illustrating reflectance and unidirectional modes of operation in accordance with an exemplary embodiment. It comprises one or more transducers 202, 204, and 206, one or more waveguides 214, and one or more optional reflecting surfaces 216. The assemblage 200 illustrates propagation of ultrasound waves 218 within the waveguide 214 in the reflectance and unidirectional modes of operation. Either ultrasound resonator or transducer 202 and 204 in combination with interfacing material or materials 208 and 210, if required, can be selected to emit ultrasound waves 218 into the waveguide 214.

In unidirectional mode, either of the ultrasound resonators or transducers can be enabled to emit ultrasound waves 218 into the waveguide 214. The non-emitting ultrasound resonator or transducer 204 is enabled to detect the ultrasound waves 218 emitted by the ultrasound resonator or transducer 202.

In reflectance mode, the ultrasound waves 218 are detected by the emitting ultrasound resonator or transducer 202 after reflecting from a surface, interface, or body at the opposite end of the waveguide 214. In this mode, either of the ultrasound resonators or transducers 202 or 204 can be selected to emit and detect ultrasound waves. Additional reflection features 216 can be added within the waveguide structure to reflect ultrasound waves. This can support operation in a combination of unidirectional and reflectance modes. In this mode of operation, one of the ultrasound resonators, for example resonator 202 is controlled to emit ultrasound waves 218 into the waveguide 214. Another ultrasound resonator or transducer 206 is controlled to detect the ultrasound waves 218 emitted by the emitting ultrasound resonator 202 (or transducer) subsequent to their reflection by reflecting feature 216.

Figure 4:
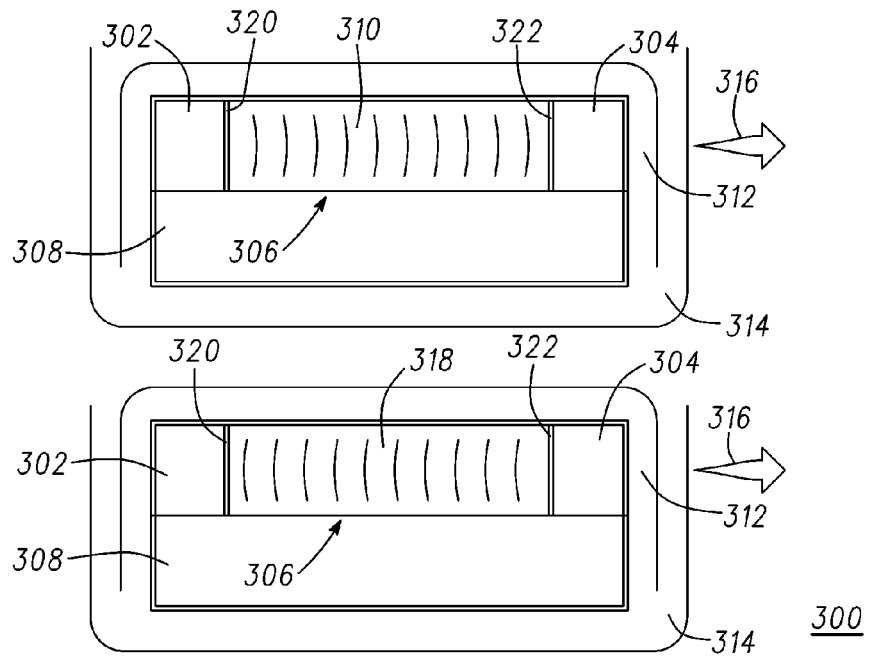
FIG. 4 is an exemplary assemblage that illustrates propagation of ultrasound waves within a waveguide in the bi-directional mode of operation of this assemblage.

FIG. 4 is an exemplary assemblage 300 that illustrates propagation of ultrasound waves 310 within the waveguide 306 in the bi-directional mode of operation of this assemblage. In this mode, the selection of the roles of the two individual ultrasound resonators (302, 304) or transducers affixed to interfacing material 320 and 322, if required, are periodically reversed. In the bi-directional mode the transit time of ultrasound waves propagating in either direction within the waveguide 306 can be measured. This can enable adjustment for Doppler effects in applications where the sensing module 308 is operating while in motion 316. Furthermore, this mode of operation helps assure accurate measurement of the applied load, force, pressure, or displacement by capturing data for computing adjustments to offset this external motion 316. An advantage is provided in situations wherein the body, instrument, appliance, vehicle, equipment, or other physical system 314, is itself operating or moving during sensing of load, pressure, or displacement. Similarly, the capability can also correct in situation where the body, instrument, appliance, vehicle, equipment, or other physical system, is causing the portion 312 of the body, instrument, appliance, vehicle, equipment, or other physical system being measured to be in motion 316 during sensing of load, force, pressure, or displacement. Other adjustments to the measurement for physical changes to system 314 are contemplated and can be compensated for in a similar fashion. For example, temperature of system 314 can be measured and a lookup table or equation having a relationship of temperature versus transit time can be used to normalize measurements. Differential measurement techniques can also be used to cancel many types of common factors as is known in the art.

The use of waveguide 306 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 5:
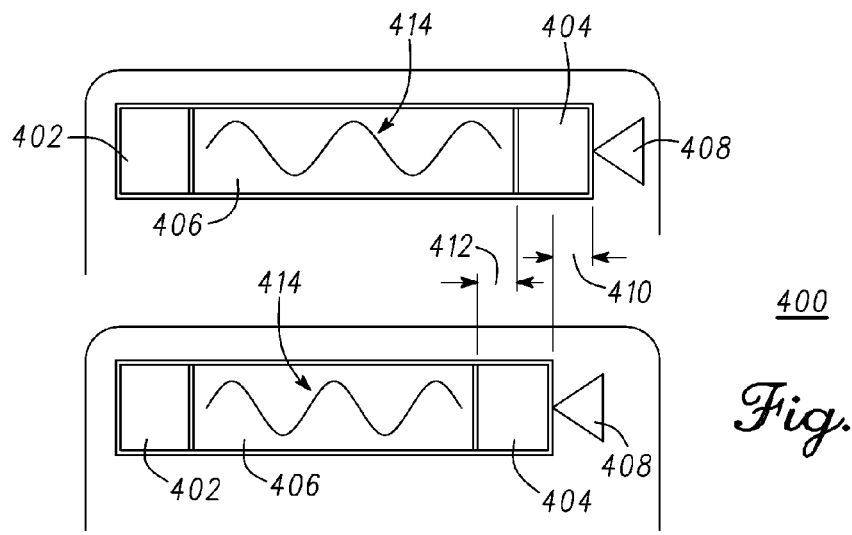
FIG. 5 is an exemplary cross-sectional view of a sensor element to illustrate changes in the propagation of ultrasound waves with changes in the length of a waveguide.

FIG. 5 is an exemplary cross-sectional view of a sensor element 400 to illustrate changes in the propagation of ultrasound waves 414 with changes in the length of a waveguide 406. In general, the measurement of a parameter is achieved by relating displacement to the parameter. In one embodiment, the displacement required over the entire measurement range is measured in microns. For example, an external force 408 compresses waveguide 406 thereby changing the length of waveguide 406. Sensing circuitry (not shown) measures propagation characteristics of ultrasonic signals in the waveguide 406 to determine the change in the length of the waveguide 406. These changes in length change in direct proportion to the parameters of interest thus enabling the conversion of changes in the parameter or parameters of interest into electrical signals.

As illustrated, external force 408 compresses waveguide 406 and pushes the transducers 402 and 404 closer to one another by a distance 410. This changes the length of waveguide 406 by distance 412 of the waveguide propagation path between transducers 402 and 404. Depending on the operating mode, the sensing circuitry measures the change in length of the waveguide 406 by analyzing characteristics of the propagation of ultrasound waves within the waveguide.

One interpretation of FIG. 5 illustrates waves emitting from transducer 402 at one end of waveguide 406 and propagating to transducer 404 at the other end of the waveguide 406. The interpretation includes the effect of movement of waveguide 406 and thus the velocity of waves propagating within waveguide 406 (without changing shape or width of individual waves) and therefore the transit time between transducers 402 and 404 at each end of the waveguide. The interpretation further includes the opposite effect on waves propagating in the opposite direction and is evaluated to estimate the velocity of the waveguide and remove it by averaging the transit time of waves propagating in both directions.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

In a continuous wave mode of operation, a phase detector (not shown) evaluates the frequency and changes in the frequency of resonant ultrasonic waves in the waveguide 406. As will be described below, positive feedback closed-loop circuit operation in continuous wave (CW) mode adjusts the frequency of ultrasonic waves 414 in the waveguide 406 to maintain a same number or integer number of periods of ultrasonic waves in the waveguide 406. The CW operation persists as long as the rate of change of the length of the waveguide is not so rapid that changes of more than a quarter wavelength occur before the frequency of the Propagation Tuned Oscillator (PTO) can respond. This restriction exemplifies one advantageous difference between the performance of a PTO and a Phase Locked Loop (PLL). Assuming the transducers are producing ultrasonic waves, for example, at 2.4 MHz, the wavelength in air, assuming a velocity of 343 microns per microsecond, is about 143 μ, although the wavelength within a waveguide may be longer than in unrestricted air.

In a pulse mode of operation, the phase detector measures a time of flight (TOF) between when an ultrasonic pulse is transmitted by transducer 402 and received at transducer 404. The time of flight determines the length of the waveguide propagating path, and accordingly reveals the change in length of the waveguide 406. In another arrangement, differential time of flight measurements (or phase differences) can be used to determine the change in length of the waveguide 406. A pulse consists of a pulse of one or more waves. The waves may have equal amplitude and frequency (square wave pulse) or they may have different amplitudes, for example, decaying amplitude (trapezoidal pulse) or some other complex waveform. The PTO is holding the phase of the leading edge of the pulses propagating through the waveguide constant. In pulse mode operation the PTO detects the leading edge of the first wave of each pulse with an edge-detect receiver rather than a zero-crossing receiver circuitry as used in CW mode.

Figure 6:
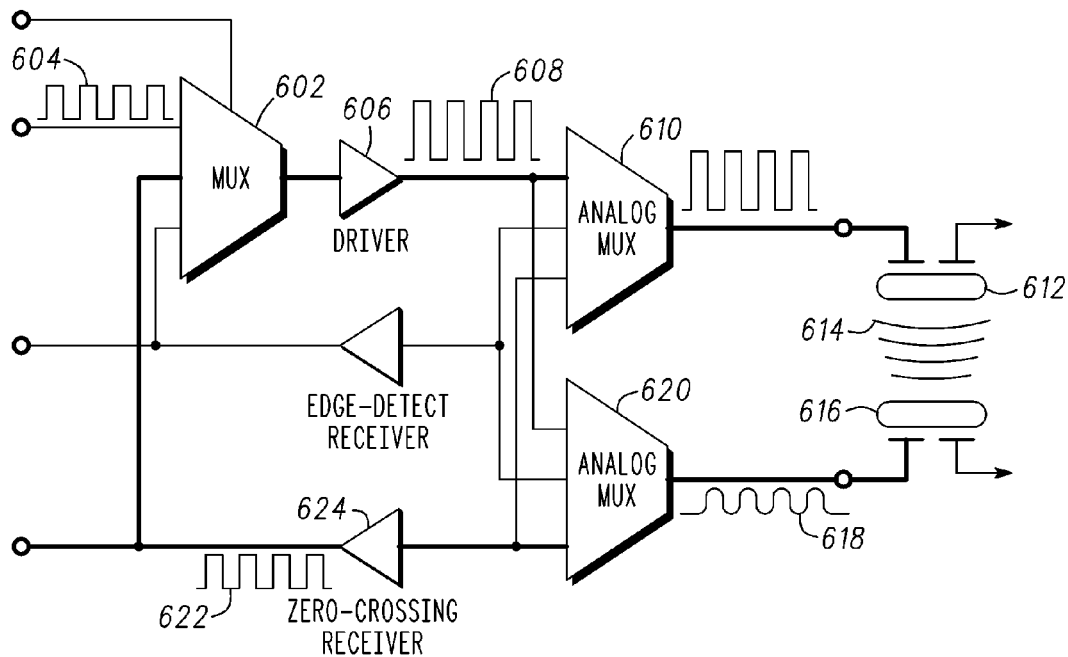
FIG. 6 is a sensor interface diagram in a continuous wave multiplexing arrangement for maintaining positive closed-loop feedback in accordance with one embodiment.

FIG. 6 is a sensor interface diagram of a continuous wave multiplexing arrangement for maintaining positive closed-loop feedback in accordance with one embodiment. The positive closed-loop feedback is illustrated by the bold line path. Initially, multiplexer (mux) 602 receives as input a clock signal 604, which is passed to the transducer driver 606 to produce the drive line signal 608. Analog multiplexer (mux) 610 receives drive line signal 608, which is passed to the transmitter transducer 612 to generate energy waves 614. Transducer 612 is located at a first location of an energy propagating medium. The emitted energy waves 614 propagate through the energy propagating medium. Receiver transducer 616 is located at a second location of the energy propagating medium. Receiver transducer 616 captures the energy waves 614, which are fed to analog mux 620 and passed to the zero-crossing receiver 624. The captured energy waves by transducer 616 are indicated by electrical waves 618 provided to mux 620. Zero-crossing receiver 624 outputs a pulse corresponding to each zero crossing detected from captured electrical waves 618. The zero crossings are counted and used to determine changes in the phase and frequency of the energy waves propagating through the energy propagating medium. In a non-limiting example, a parameter such as applied force is measured by relating the measured phase and frequency to a known relationship between the parameter (e.g. force) and the material properties of the energy propagating medium. In general, pulse sequence 622 corresponds to the detected signal frequency. The transducer driver 606 and the zero-crossing receiver 624 are in a feedback path of the propagation tuned oscillator. The pulse sequence 622 is coupled through mux 602 in a positive closed-loop feedback path. The pulse sequence 622 disables the clock signal 604 such that the path providing pulse sequence 622 is coupled to transducer driver 606 to continue emission of energy waves into the energy propagating medium and the path of clock signal 604 to driver 606 is disabled.

Figure 7:
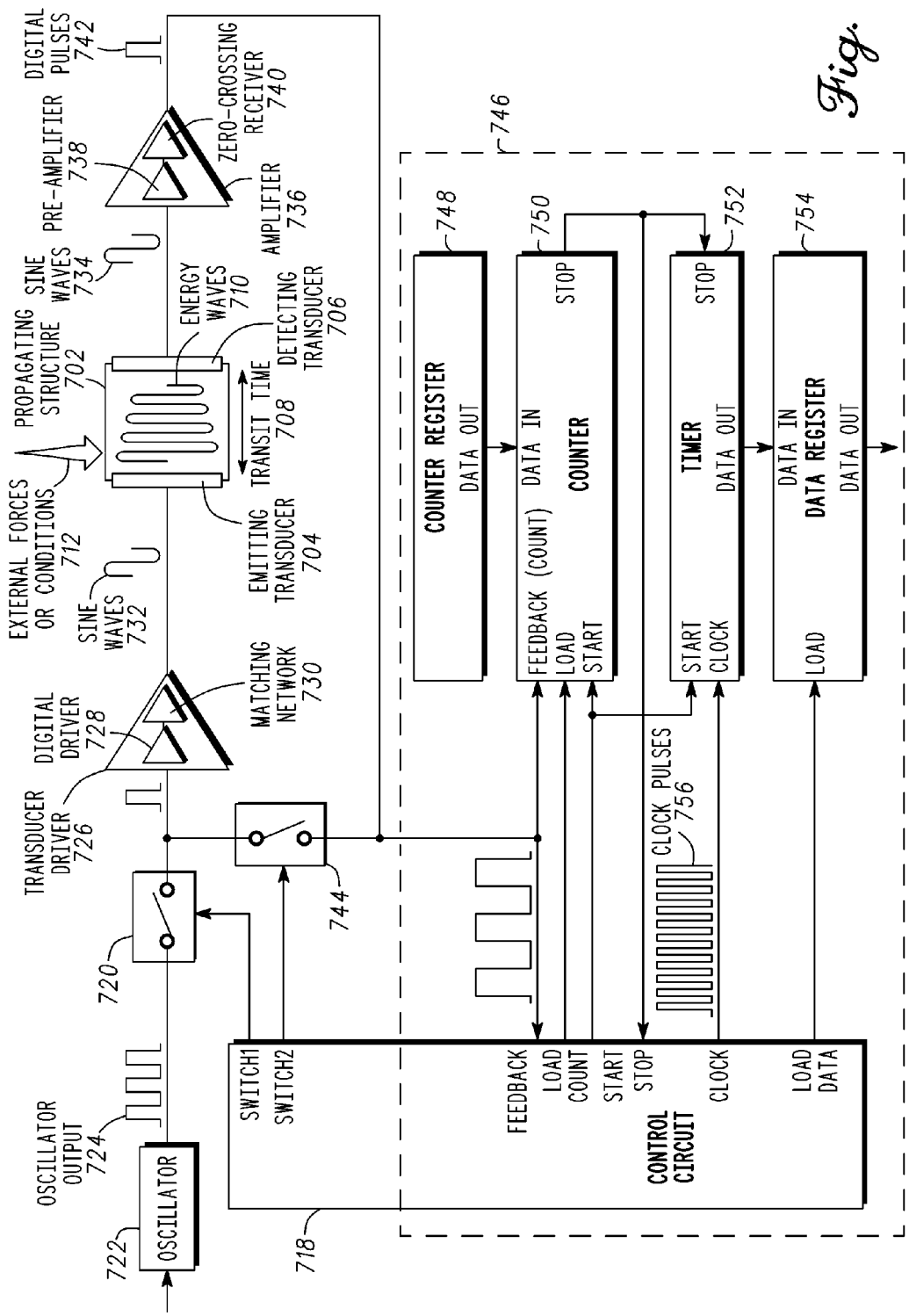
FIG. 7 is an exemplary block diagram of a propagation tuned oscillator (PTO) for operation in continuous wave mode.

FIG. 7 is an exemplary block diagram of a propagation tuned oscillator (PTO) incorporating for operation in continuous wave mode. The diagram illustrates closed loop measurement of a transit time 708 of ultrasound waves within propagating structure 702 by the operation of the propagation tuned oscillator. This example is for operation in continuous wave mode. The system can also be operated in pulse mode and a pulse-echo mode. Pulse mode and pulsed echo-mode use a pulsed energy wave. Pulse-echo mode uses reflection to direct an energy wave within the energy propagation medium. Briefly, the digital logic circuit 746 digitizes the frequency of operation of the propagation tuned oscillator.

In continuous wave mode of operation a sensor comprising transducer 704, propagating structure 702, and transducer 706 is used to measure the parameter. In general, the parameter to be measured affects the properties of the propagating medium. For example, an external force or condition 712 is applied to propagating structure 702 that changes the length of the waveguide in a path of a propagating energy wave. A change in length corresponds to a change in transit time 708 of the propagating wave. Similarly, the length of propagating structure 702 corresponds to the applied force 712. A length reduction corresponds to a higher force being applied to the propagating structure 702. Conversely, a length increase corresponds to a lowering of the applied force 712 to the propagating structure 702. The length of propagating structure 702 is measured and is converted to force by way of a known length to force relationship.

Transducer 704 is an emitting device in continuous wave mode. The sensor for measuring a parameter comprises transducer 704 coupled to propagating structure 702 at a first location. A transducer 706 is coupled to propagating structure 702 at a second location. Transducer 706 is a receiving transducer for capturing propagating energy waves. In one embodiment, the captured propagated energy waves are electrical sine waves 734 that are output by transducer 706.

A measurement sequence is initiated when control circuitry 718 closes switch 720 coupling oscillator output 724 of oscillator 722 to the input of transducer driver 726. One or more pulses provided to transducer driver 726 initiates an action to propagate energy waves 710 having simple or complex waveforms through energy propagating structure or medium 702. Transducer driver 726 comprises a digital driver 728 and matching network 730. In one embodiment, transducer driver 726 transforms the oscillator output of oscillator 722 into sine waves of electrical waves 732 having the same repetition rate as oscillator output 724 and sufficient amplitude to excite transducer 704.

Emitting transducer 704 converts the sine waves 732 into energy waves 710 of the same frequency and emits them at the first location into energy propagating structure or medium 702. The energy waves 710 propagate through energy propagating structure or medium 702. Upon reaching transducer 706 at the second location, energy waves 710 are captured, sensed, or detected. The captured energy waves are converted by transducer 706 into sine waves 734 that are electrical waves having the same frequency.

Amplifier 736 comprises a pre-amplifier 738 and zero-cross receiver 740. Amplifier 736 converts the sine waves 734 into digital pulses 742 of sufficient duration to sustain the behavior of the closed loop circuit. Control circuitry 718 responds to digital pulses 742 from amplifier 736 by opening switch 720 and closing switch 744. Opening switch 720 decouples oscillator output 724 from the input of transducer driver 726. Closing switch 744 creates a closed loop circuit coupling the output of amplifier 736 to the input of transducer driver 726 and sustaining the emission, propagation, and detection of energy waves through energy propagating structure or medium 702.

An equilibrium state is attained by maintaining unity gain around this closed loop circuit wherein sine waves 732 input into transducer 704 and sine waves 734 output by transducer 706 are in phase with a small but constant offset. Transducer 706 as disclosed above, outputs the sine waves 734 upon detecting energy waves propagating to the second location. In the equilibrium state, an integer number of energy waves 710 propagate through energy propagating structure or medium 702.

Movement or changes in the physical properties of energy propagating structure or medium 702 change a transit time 708 of energy waves 710. The transit time 708 comprises the time for an energy wave to propagate from the first location to the second location of propagating structure 702. Thus, the change in the physical property of propagating structure 702 results in a corresponding time period change of the energy waves 710 within energy propagating structure or medium 702. These changes in the time period of the energy waves 710 alter the equilibrium point of the closed loop circuit and frequency of operation of the closed loop circuit. The closed loop circuit adjusts such that sine waves 732 and 734 correspond to the new equilibrium point. The frequency of energy waves 710 and changes to the frequency correlate to changes in the physical attributes of energy propagating structure or medium 702.

The physical changes may be imposed on energy propagating structure 702 by external forces or conditions 712 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 710 during the operation of the closed loop circuit, and changes in this frequency, may be used to measure movement or changes in physical attributes of energy propagating structure or medium 702.

Prior to measurement of the frequency or operation of the propagation tuned oscillator, control logic 718 loads the loop count into digital counter 750 that is stored in count register 748. The first digital pulses 742 initiates closed loop operation within the propagation tuned oscillator and signals control circuit 718 to start measurement operations. At the start of closed loop operation, control logic 718 enables digital counter 750 and digital timer 752. In one embodiment, digital counter 750 decrements its value on the rising edge of each digital pulse output by zero-cross receiver 740. Digital timer 752 increments its value on each rising edge of clock pulses 756. When the number of digital pulses 742 has decremented, the value within digital counter 750 to zero a stop signal is output from digital counter 750. The stop signal disables digital timer 752 and triggers control circuit 718 to output a load command to data register 754. Data register 754 loads a binary number from digital timer 752 that is equal to the period of the energy waves or pulses times the value in counter 748 divided by clock period 756. With a constant clock period 756, the value in data register 754 is directly proportional to the aggregate period of the energy waves or pulses accumulated during the measurement operation. Duration of the measurement operation and the resolution of measurements may be adjusted by increasing or decreasing the value preset in the count register 748.

In general, the initial frequency of the PTO is driven by oscillator 722. Closing the loop once the initial waves are detected by the second amplifier will tune the PTO to the nearest whole wavelength around the entire feedback loop. An integer number of wavelengths will be propagating through the waveguide, less the delay through the transducers and electronic circuitry and interconnect. As mentioned previously, these other delays may be much shorter than the propagation delay through the waveguide and that they are essentially constant. At maximum compression, a waveguide is shortened by essentially no more than 200 microns and this may be on the order of a wavelength of ultrasound at an operating frequency of 2.4 MHz. Change in length is very unlikely to occur in a time span comprising microseconds. Under these conditions, restriction of the operation of the PTO is less a constraint and the frequency of oscillation will track changes in the length of the waveguide. In this configuration the PTO is holding the phase of the waves emitted by transducer 704 close to the phase of the analog waves detected by transducer 706 by detecting the zero-crossing point of the detected waves. As long as there is not too large a discontinuity in the change in the length of the waveguide, holding the phase relationship constant will hold the number of wavelengths within the waveguide constant. Accordingly, a change in frequency of the ultrasonic waves can be measured by electronic circuitry and directly related (proportional) to the (changing) length of the waveguide or propagating structure 702.

The change of frequency of the feedback loop is continuous over changes in distance, within the settling time of the propagation tuned oscillator, between the emitting or transmitting transducer and the detecting or receiving transducer are less than a wavelength.

Figure 8:
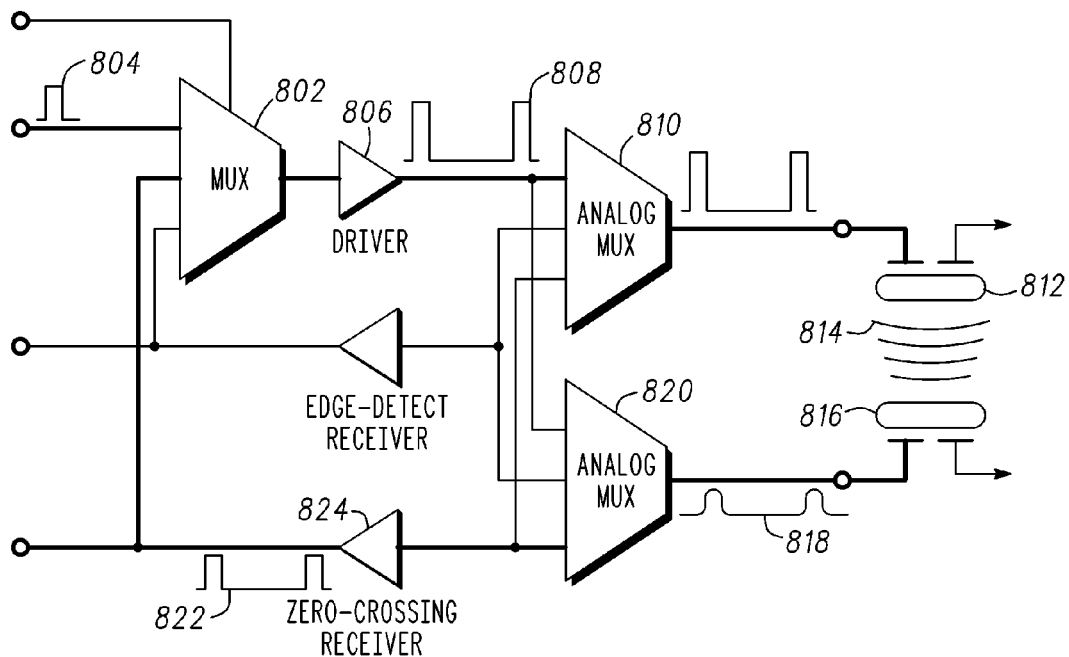
FIG. 8 is a sensor interface diagram in a pulse multiplexing arrangement for maintaining positive closed-loop feedback in accordance with one embodiment.

FIG. 8 is a sensor interface diagram in a pulse multiplexing arrangement for maintaining positive closed-loop feedback in accordance with one embodiment. In one embodiment, the circuitry other than the sensor is integrated on an application specific integrated circuit (ASIC). The positive closed-loop feedback is illustrated by the bold line path. Initially, mux 802 is enabled to couple one or more digital pulses 804 to the transducer driver 806. Transducer driver 806 generates a pulse sequence 808 corresponding to digital pulses 804. Analog mux 810 is enabled to couple pulse sequence 808 to the transmitter transducer 812. Transducer 812 is coupled to a medium at a first location. Transducer 812 responds to pulse sequence 808 and generates corresponding energy pulses 814 that are emitted into the medium at the first location. The energy pulses 814 propagate through the medium. A receiver transducer 816 is located at a second location on the medium. Receiver transducer 816 captures the energy pulses 814 and generates a corresponding signal of electrical pulses 818. Transducer 816 is coupled to a mux 820. Mux 820 is enabled to couple to zero-cross receiver 824. Electrical pulses 818 from transducer 816 are coupled to zero-cross receiver 824. Zero-cross receiver 824 counts zero crossings of electrical pulses 818 to determine changes in phase and frequency of the energy pulses responsive to an applied force, as previously explained. Zero-cross receiver 824 outputs a pulse sequence 822 corresponding to the detected signal frequency. Pulse sequence 822 is coupled to mux 802. Mux 802 is decoupled from coupling digital pulses 804 to driver 806 upon detection of pulses 822. Conversely, mux 802 is enabled to couple pulses 822 to driver 806 upon detection of pulses 822 thereby creating a positive closed-loop feedback path. Thus, in pulse mode, transducer driver 806 and zero-cross receiver 824 is part of the closed-loop feedback path that continues emission of energy pulses into the medium at the first location and detection at the second location to measure a transit time and changes in transit time of pulses through the medium.

FIG. 9 is an exemplary block diagram of a propagation tuned oscillator (PTO) for operation in pulse mode. It illustrates closed loop measurement of a transit time 708 of ultrasound pulsed waves within the energy propagating structure 702 by the operation of the propagation tuned oscillator. This example is for operation in pulse mode. The system can also be operated in continuous wave mode and a pulse-echo mode. Continuous wave mode uses a continuous wave signal. Pulse-echo mode uses reflection to direct an energy wave within the energy propagation medium. Briefly, the digital logic circuit 746 digitizes the frequency of operation of the propagation tuned oscillator.

In pulse mode of operation, a sensor comprising transducer 704, propagating structure 702, and transducer 706 is used to measure the parameter. In general, the parameter to be measured affects the properties of the propagating medium. For example, an external force or condition 712 is applied to propagating structure 702 that changes the length of the waveguide in a path of a propagating energy wave. A change in length corresponds to a change in transit time 708 of the propagating wave. The length of propagating structure 702 is measured and is converted to force by way of a known length to force relationship. One benefit of pulse mode operation is the use of a high magnitude pulsed energy wave. In one embodiment, the magnitude of the energy wave decays as it propagates through the medium. The use of a high magnitude pulse is a power efficient method to produce a detectable signal if the energy wave has to traverse a substantial distance or is subject to a reduction in magnitude as it propagated due to the medium.

A measurement sequence is initiated when control circuitry 718 closes switch 720 coupling oscillator output 724 of oscillator 722 to the input of transducer driver 726. One or more pulses provided to transducer driver 726 initiates an action to propagate energy waves 710 having simple or complex waveforms through energy propagating structure or medium 702. Transducer driver 726 comprises a digital driver 728 and matching network 730. In one embodiment, transducer driver 726 transforms the oscillator output of oscillator 722 into analog pulses of electrical waves 932 having the same repetition rate as oscillator output 724 and sufficient amplitude to excite transducer 704.

Emitting transducer 704 converts the analog pulses 932 into energy waves 710 of the same frequency and emits them at a first location into energy propagating structure or medium 702. The energy waves 710 propagate through energy propagating structure or medium 702. Upon reaching transducer 706 at the second location, energy waves 710 are captured, sensed, or detected. The captured energy waves are converted by transducer 706 into analog pulses 934 that are electrical waves having the same frequency.

Amplifier 736 comprises a pre-amplifier 738 and zero-cross receiver 740. Amplifier 736 converts the analog pulses 934 into digital pulses 742 of sufficient duration to sustain the behavior of the closed loop circuit. Control circuitry 718 responds to digital pulses 742 from amplifier 736 by opening switch 720 and closing switch 744. Opening switch 720 decouples oscillator output 724 from the input of transducer driver 726. Closing switch 744 creates a closed loop circuit coupling the output of amplifier 736 to the input of transducer driver 726 and sustaining the emission, propagation, and detection of energy waves through energy propagating structure or medium 702.

An equilibrium state is attained by maintaining unity gain around this closed loop circuit wherein pulses 932 input into transducer 704 and pulses 934 output by transducer 706 are in phase with a small but constant offset. Transducer 706 as disclosed above, outputs the pulses 934 upon detecting energy waves propagating to the second location. In the equilibrium state, an integer number of energy waves 710 propagate through energy propagating structure or medium 702.

Movement or changes in the physical properties of energy propagating structure or medium 702 change a transit time 708 of energy waves 710. The transit time 708 comprises the time for an energy wave to propagate from the first location to the second location of propagating structure 702. Thus, the change in the physical property of propagating structure 702 results in a corresponding time period change of the energy waves 710 within energy propagating structure or medium 702. These changes in the time period of the energy waves 710 alter the equilibrium point of the closed loop circuit and frequency of operation of the closed loop circuit. The closed loop circuit adjusts such that pulses 932 and 934 correspond to the new equilibrium point. The frequency of energy waves 710 and changes to the frequency correlate to changes in the physical attributes of energy propagating structure or medium 702.

The physical changes may be imposed on energy propagating structure 702 by external forces or conditions 712 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest as disclosed in more detail hereinabove. Similarly, the frequency of energy waves 710 during the operation of the closed loop circuit, and changes in this frequency, may be used to measure movement or changes in physical attributes of energy propagating structure or medium 702.

For pulses of energy or ultrasound waves to be distinguishable, the repetition rates of pulses of energy or ultrasound waves will be lower than the frequency of the waves within each pulse. In some embodiments of propagation tuned oscillators, the emitting or transmitting transducer may generate several waves of ultrasound energy whenever it is pulsed. In this case stable operation of the propagation tuned oscillator may require that the number of waves propagating thought the waveguide be long enough that the waves within the pulse damp out during propagation through the waveguide The electrical portion of the feedback loop of an embodiment of a propagation tuned oscillator may be inverting or non-inverting. If non-inverting an integer number of wavelengths will be propagating within the waveguide or propagation medium at equilibrium. If the electrical portion of the feedback loop is inverting, there will be an integer number plus one-half wavelength propagating within the waveguide or propagation medium at equilibrium. The electrical portion of the feedback loop may be designed so either inverting or non-inverting operation is selectable.

Figure 12:
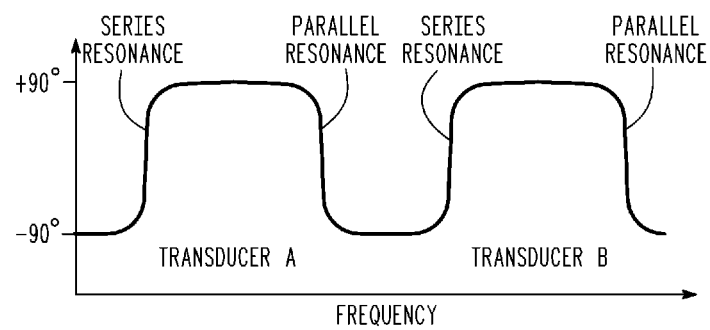
FIG. 12 is an illustration of a plot of non-overlapping resonant frequencies of paired transducers in accordance with an exemplary embodiment.

Briefly referring to FIG. 12, an exemplary plot of non-overlapping resonant frequencies of paired transducers is shown. One approach to avoiding operation where the frequency of operation of a propagation tuned oscillator is bound this way is to select transducers with different resonant frequencies. The two transducers are selected such that their respective series and parallel resonant frequencies do not overlap. That is, that both resonant frequencies of one transducer are higher than either resonant frequency of the other transducer.

Figure 10:
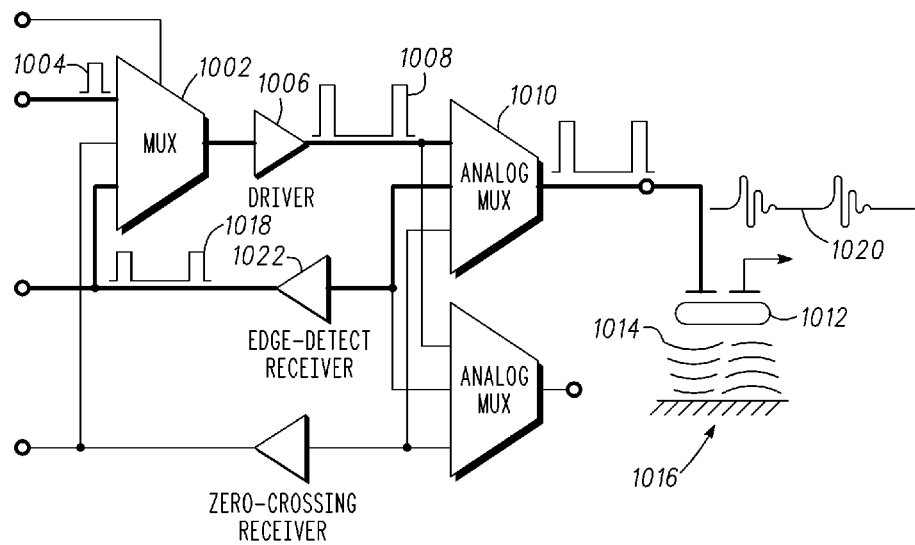
FIG. 10 is a sensor interface diagram in a pulse-echo multiplexing arrangement for maintaining positive closed-loop feedback in accordance with one embodiment.

FIG. 10 is a sensor interface diagram in a pulse-echo multiplexing arrangement for maintaining positive closed-loop feedback in accordance with one embodiment. The positive closed-loop feedback is illustrated by the bold line path. Initially, multiplexer (mux) 1002 receives as input a digital pulse 1004, which is passed to the transducer driver 1006 to produce the pulse sequence 1008. Analog multiplexer (mux) 1010 receives pulse sequence 1008, which is passed to the transducer 1012 to generate energy pulses 1014. Energy pulses 1014 are emitted into a first location of a medium and propagate through the medium. In the pulse-echo example, energy pulses 1014 are reflected off a surface 1016 at a second location of the medium, for example, the end of a waveguide or reflector, and echoed back to the transducer 1012. The transducer 1012 proceeds to capture the reflected pulse echo. In pulsed echo mode, the transducer 1012 performs as both a transmitter and a receiver. As disclosed above, transducer 1012 toggles back and forth between emitting and receiving energy waves. Transducer 1012 captures the reflected echo pulses, which are coupled to analog mux 1010 and directed to the edge-detect receiver 1022. The captured reflected echo pulses are indicated by electrical waves 1018. Edge-detect receiver 1022 locks on pulse edges corresponding to the wave front of a propagated energy wave to determine changes in phase and frequency of the energy pulses 1014 responsive to an applied force, as previously explained. Among other parameters, it generates a pulse sequence 1018 corresponding to the detected signal frequency. The pulse sequence 1018 is coupled to mux 1002 and directed to driver 1006 to initiate one or more energy waves being emitted into the medium by transducer 1012. Pulse 1004 is decoupled from being provided to driver 1006. Thus, a positive closed loop feedback including transducer driver 1006 is formed that repeatably emits energy waves into the medium until mux 1002 prevents a signal from being provided to driver 1006. The edge-detect receiver 1022 is coupled to a second location of the medium and is in the feedback path. The edge-detect receiver 1002 initiates a pulsed energy wave being provided at the first location of the medium upon detecting a wave front at the second location when the feedback path is closed.

Figure 11:
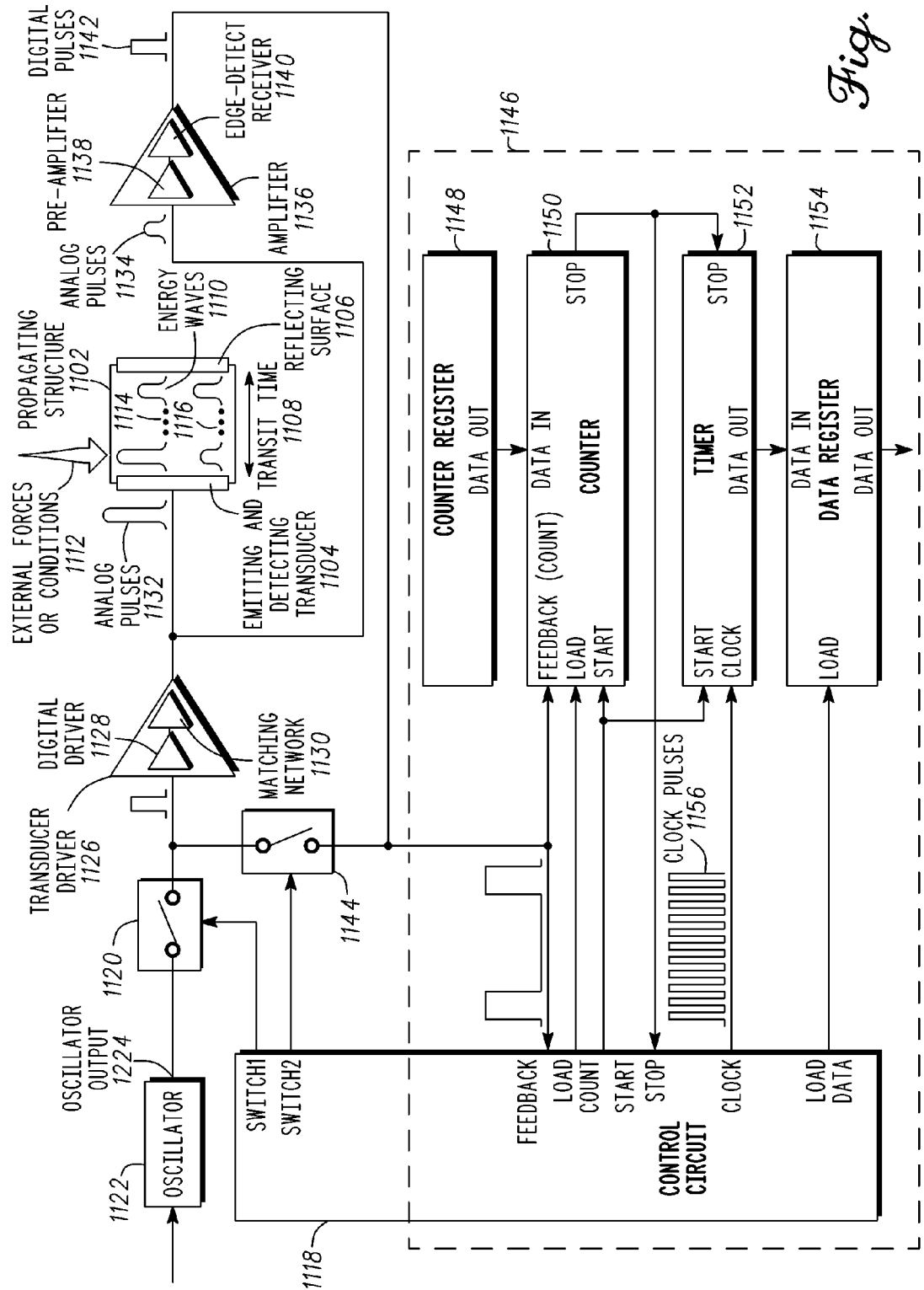
FIG. 11 is an exemplary block diagram of a propagation tuned oscillator (PTO) in pulse echo mode in accordance with an exemplary embodiment.

FIG. 11 is an exemplary block diagram of a propagation tuned oscillator (PTO) in pulse echo mode in accordance with an exemplary embodiment. It illustrates closed loop measurement of a transit time 1108 of ultrasound waves 1110 within an energy propagating structure 1103 by the operation of the propagation tuned oscillator. This example is for operation in a pulse echo mode. The system can also be operated in pulse mode and a continuous wave mode. Pulse mode does not use a reflected signal. Continuous wave mode uses a continuous signal. Briefly, the digital logic circuit 1146 digitizes the frequency of operation of the propagation tuned oscillator.

In pulse-echo mode of operation a sensor comprising transducer 1104, propagating structure 1102, and reflecting surface 1106 is used to measure the parameter. In general, the parameter to be measured affects the properties of the propagating medium. For example, an external force or condition 1112 is applied to propagating structure 1102 that changes the length of the waveguide in a path of a propagating energy wave. A change in length corresponds to a change in transit time of the propagating wave. Similarly, the length of propagating structure 1102 corresponds to the applied force 1112. A length reduction corresponds to a higher force being applied to the propagating structure 1102. Conversely, a length increase corresponds to a lowering of the applied force 1112 to the propagating structure 1102. The length of propagating structure 1102 is measured and is converted to force by way of a known length to force relationship.

Transducer 1104 is both an emitting device and a receiving device in pulse-echo mode. The sensor for measuring a parameter comprises transducer 1104 coupled to propagating structure 1102 at a first location. A reflecting surface is coupled to propagating structure 1102 at a second location. Transducer 1104 has two modes of operation comprising an emitting mode and receiving mode. Transducer 1104 emits an energy wave into the propagating structure 1102 at the first location in the emitting mode. The energy wave propagates to a second location and is reflected by reflecting surface 1106. The reflected energy wave is reflected towards the first location and transducer 1104 subsequently generates a signal in the receiving mode corresponding to the reflected energy wave.

A measurement sequence in pulse echo mode is initiated when control circuitry 1118 closes switch 1120 coupling digital output 1124 of oscillator 1122 to the input of transducer driver 1126. One or more pulses provided to transducer driver 1126 starts a process to emit one or more energy waves 1110 having simple or complex waveforms into energy propagating structure or medium 1102. Transducer driver 1126 comprises a digital driver 1128 and matching network 1130. In one embodiment, transducer driver 1126 transforms the digital output of oscillator 1122 into pulses of electrical waves 1132 having the same repetition rate as digital output 1124 and sufficient amplitude to excite transducer 1104.

Transducer 1104 converts the pulses of electrical waves 1132 into pulses of energy waves 1110 of the same repetition rate and emits them into energy propagating structure or medium 1102. The pulses of energy waves 1110 propagate through energy propagating structure or medium 1102 as shown by arrow 1114 towards reflecting surface 1106. Upon reaching reflecting surface 1106, energy waves 1110 are reflected by reflecting surface 1106. Reflected energy waves propagate towards transducer 1104 as shown by arrow 1116. The reflected energy waves are detected by transducer 1104 and converted into pulses of electrical waves 1134 having the same repetition rate.

Amplifier 1136 comprises a pre-amplifier 1138 and edge-detect receiver 1140. Amplifier 1136 converts the pulses of electrical waves 1134 into digital pulses 1142 of sufficient duration to sustain the pulse behavior of the closed loop circuit. Control circuitry 1118 responds to digital output pulses 1142 from amplifier 1136 by opening switch 1120 and closing switch 1144. Opening switch 1120 decouples oscillator output 1124 from the input of transducer driver 1126. Closing switch 1144 creates a closed loop circuit coupling the output of amplifier 1136 to the input of transducer driver 1126 and sustaining the emission, propagation, and detection of energy pulses through energy propagating structure or medium 1102.

An equilibrium state is attained by maintaining unity gain around this closed loop circuit wherein electrical waves 1132 input into transducer 1104 and electrical waves 1134 output by transducer 1104 are in phase with a small but constant offset. Transducer 1104 as disclosed above, outputs the electrical waves 1134 upon detecting reflected energy waves reflected from reflecting surface 1106. In the equilibrium state, an integer number of pulses of energy waves 1110 propagate through energy propagating structure or medium 1102.

Movement or changes in the physical properties of energy propagating structure or medium 1102 change a transit time 1108 of energy waves 1110. The transit time 1108 comprises the time for an energy wave to propagate from the first location to the second location of propagating structure 1102 and the time for the reflected energy wave to propagate from the second location to the first location of propagating structure 1102. Thus, the change in the physical property of propagating structure 1102 results in a corresponding time period change of the energy waves 1110 within energy propagating structure or medium 1102. These changes in the time period of the repetition rate of the energy pulses 1110 alter the equilibrium point of the closed loop circuit and repetition rate of operation of the closed loop circuit. The closed loop circuit adjusts such that electrical waves 1132 and 1134 correspond to the new equilibrium point. The repetition rate of energy waves 1110 and changes to the repetition rate correlate to changes in the physical attributes of energy propagating structure or medium 1102.

The physical changes may be imposed on energy propagating structure 1102 by external forces or conditions 1112 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 1110 during the operation of the closed loop circuit, and changes in this frequency, may be used to measure movement or changes in physical attributes of energy propagating structure or medium 1102.

Prior to measurement of the frequency or operation of the propagation tuned oscillator, control logic 1118 loads the loop count into digital counter 1150 that is stored in count register 1148. The first digital pulses 1142 initiates closed loop operation within the propagation tuned oscillator and signals control circuit 1118 to start measurement operations. At the start of closed loop operation, control logic 1118 enables digital counter 1150 and digital timer 1152. In one embodiment, digital counter 1150 decrements its value on the rising edge of each digital pulse output by edge-detect receiver 1140. Digital timer 1152 increments its value on each rising edge of clock pulses 1156. When the number of digital pulses 1142 has decremented, the value within digital counter 1150 to zero a stop signal is output from digital counter 1150. The stop signal disables digital timer 1152 and triggers control circuit 1118 to output a load command to data register 1154. Data register 1154 loads a binary number from digital timer 1152 that is equal to the period of the energy waves or pulses times the value in counter 1148 divided by clock period 1156. With a constant clock period 1156, the value in data register 1154 is directly proportional to the aggregate period of the energy waves or pulses accumulated during the measurement operation. Duration of the measurement operation and the resolution of measurements may be adjusted by increasing or decreasing the value preset in the count register 1148.

FIG. 12 is an illustration of a plot of non-overlapping resonant frequencies of paired transducers in accordance with an exemplary embodiment. In a non-limiting example, the characteristics of transducer A correspond to a first transducer driven by a transducer driver circuit as disclosed herein. The first transducer emits an energy wave into a medium at a first location. The characteristics of transducer B correspond to a second transducer for receiving a propagated energy wave. Transducer B outputs a signal corresponding to the propagated energy wave. Operation too close to their resonant frequencies results in substantial changes in phase, but limits shifts in frequency with changes in propagation through the waveguide or propagation medium. One approach to avoiding operation where the frequency of operation of an embodiment of a propagation tuned oscillator is bound this way is to select transducers with different resonant frequencies. The two transducers may be selected such that their respective series and parallel resonant frequencies do not overlap. That is, that both resonant frequencies of one transducer must be higher than either resonant frequency of the other transducer. This approach has the benefit of substantial, monotonic shifts in operating frequency of the present embodiment of a propagation tuned oscillator with changes in the transit time of energy or ultrasound waves within the waveguide or propagation medium with minimal signal processing, electrical components, and power consumption Measurement of the changes in the physical length of individual ultrasound waveguides may be made in several modes. Each assemblage of one or two ultrasound resonators or transducers combined with an ultrasound waveguide may be controlled to operate in six different modes. This includes two wave shape modes: continuous wave or pulsed waves, and three propagation modes: reflectance, unidirectional, and bidirectional propagation of the ultrasound wave. The resolution of these measurements can be further enhanced by advanced processing of the measurement data to enable optimization of the trade-offs between measurement resolution versus length of the waveguide, frequency of the ultrasound waves, and the bandwidth of the sensing and data capture operations, thus achieving an optimal operating point for a sensing module or device.

Figure 13:
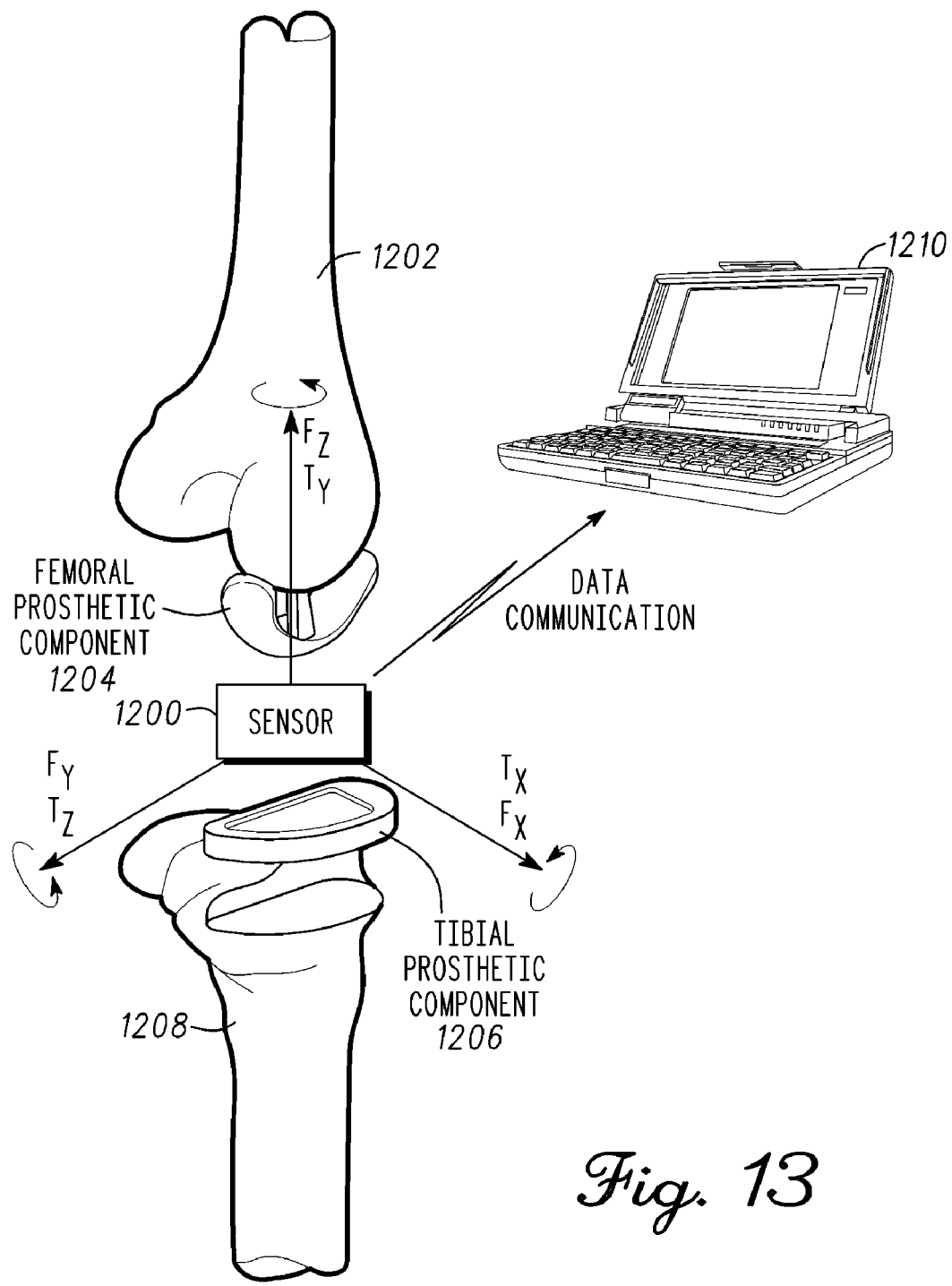
FIG. 13 is an illustration of a sensor placed in contact between a femur and a tibia for measuring a parameter in accordance with an exemplary embodiment.

FIG. 13 is an illustration of a sensor 1200 placed in contact between a femur 1202 and a tibia 1208 for measuring a parameter in accordance with an exemplary embodiment. In general, a sensor 1200 is placed in contact with or in proximity to the muscular-skeletal system to measure a parameter. In a non-limiting example, sensor 1200 can be operated in continuous wave mode, pulse mode, and pulse echo-mode to measure a parameter of a joint or an artificial joint. Embodiments of sensor 1200 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Sensor 1200 can provide implant status data to the orthopedic manufacturers and surgeons. Moreover, data generated by direct measurement of the implanted joint itself would greatly improve the knowledge of implanted joint operation and joint wear thereby leading to improved design and materials.

In at least one exemplary embodiment, an energy pulse is directed within one or more waveguides in sensor 1200 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

Sensor 1200 can be size constrained by form factor requirements of fitting within a region the muscular-skeletal system or a component such as a tool, equipment, or artificial joint. In a non-limiting example, sensor 1200 is used to measure load and balance of an installed artificial knee joint. A knee prosthesis comprises a femoral prosthetic component 1204, an insert, and a tibial prosthetic component 1206. A distal end of femur 1202 is prepared and receives femoral prosthetic component 1204. Femoral prosthetic component 1204 typically has two condyle surfaces that mimic a natural femur. As shown, femoral prosthetic component 1204 has single condyle surface being coupled to femur 1202. Femoral prosthetic component 1204 is typically made of a metal or metal alloy.

A proximal end of femur 1208 is prepared to receive tibial prosthetic component 1206. Tibial prosthetic component 1206 is a support structure that is fastened to the proximal end of the tibia and is usually made of a metal or metal alloy. The tibial prosthetic component 1206 also retains the insert in a fixed position with respect to femur 1208. The insert is fitted between femoral prosthetic component 1204 and tibial prosthetic component 1206. The insert has at least one bearing surface that is in contact with at least condyle surface of femoral prosthetic component 1204. The condyle surface can move in relation to the bearing surface of the insert such that the lower leg can rotate under load. The insert is typically made of a high wear plastic material that minimizes friction.

In a knee joint replacement process, the surgeon affixes femoral prosthetic component 1204 to the femur 1202 and tibial prosthetic component 1206 to femur 1208. The tibial prosthetic component 1206 can include a tray or plate affixed to the planarized proximal end of the femur 1208. Sensor 1200 is placed between a condyle surface of femoral prosthetic component 1204 and a major surface of tibial prosthetic component 1206. The condyle surface contacts a major surface of sensor 1200. The major surface of sensor 1200 approximates a surface of the insert. Tibial prosthetic component 1206 can include a cavity or tray on the major surface that receives and retains sensor 1200 during a measurement process. Tibial prosthetic component 1206 and sensor 1200 has a combined thickness that represents a combined thickness of tibial prosthetic component 1206 and a final (or chronic) insert of the knee joint.

In one embodiment, two sensors 1200 are fitted into two separate cavities, the cavities are within a trial insert (that may also be referred to as the tibial insert, rather than the tibial component itself) that is held in position by tibial component 1206. One or two sensors 1200 may be inserted between femoral prosthetic component 1204 and tibial prosthetic component 1206. Each sensor is independent and each measures a respective condyle of femur 1202. Separate sensors also accommodate a situation where a single condyle is repaired and only a single sensor is used. Alternatively, the electronics can be shared between two sensors to lower cost and complexity of the system. The shared electronics can multiplex between each sensor module to take measurements when appropriate. Measurements taken by sensor 1200 aid the surgeon in modifying the absolute loading on each condyle and the balance between condyles. Although shown for a knee implant, sensor 1200 can be used to measure other orthopedic joints such as the spine, hip, shoulder, elbow, ankle, wrist, interphalangeal joint, metatarsophalangeal joint, metacarpophalangeal joints, and others. Alternatively, sensor 1200 can also be adapted to orthopedic tools to provide measurements.

The prosthesis incorporating sensor 1200 emulates the function of a natural knee joint. Sensor 1200 can measure loads or other parameters at various points throughout the range of motion. Data from sensor 1200 is transmitted to a receiving station 1210 via wired or wireless communications. In a first embodiment, sensor 1200 is a disposable system. Sensor 1200 can be disposed of after using sensor 1200 to optimally fit the joint implant. Sensor 1200 is a low cost disposable system that reduces capital costs, operating costs, facilitates rapid adoption of quantitative measurement, and initiates evidentiary based orthopedic medicine. In a second embodiment, a methodology can be put in place to clean and sterilize sensor 1200 for reuse. In a third embodiment, sensor 1200 can be incorporated in a tool instead of being a component of the replacement joint. The tool can be disposable or be cleaned and sterilized for reuse. In a fourth embodiment, sensor 1200 can be a permanent component of the replacement joint. Sensor 1200 can be used to provide both short term and long term post-operative data on the implanted joint. In a fifth embodiment, sensor 1200 can be coupled to the muscular-skeletal system. In all of the embodiments, receiving station 1210 can include data processing, storage, or display, or combination thereof and provide real time graphical representation of the level and distribution of the load. Receiving station 1210 can record and provide accounting information of sensor 1200 to an appropriate authority.

In an intra-operative example, sensor 1200 can measure forces (Fx, Fy, Fz) with corresponding locations and torques (e.g. Tx, Ty, and Tz) on the femoral prosthetic component 1204 and the tibial prosthetic component 1206. The measured force and torque data is transmitted to receiving station 1210 to provide real-time visualization for assisting the surgeon in identifying any adjustments needed to achieve optimal joint pressure and balancing. The data has substantial value in determining ranges of load and alignment tolerances required to minimize rework and maximize patient function and longevity of the joint.

As mentioned previously, sensor 1200 can be used for other joint surgeries; it is not limited to knee replacement implant or implants. Moreover, sensor 1200 is not limited to trial measurements. Sensor 1200 can be incorporated into the final joint system to provide data post-operatively to determine if the implanted joint is functioning correctly. Early determination of a problem using sensor 1200 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, sensor 1200 can be shaped such that it can be placed or engaged or affixed to or within load bearing surfaces used in many orthopedic applications (or used in any orthopedic application) related to the musculoskeletal system, joints, and tools associated therewith. Sensor 1200 can provide information on a combination of one or more performance parameters of interest such as wear, stress, kinematics, kinetics, fixation strength, ligament balance, anatomical fit and balance.

The present invention is applicable to a wide range of medical and nonmedical applications including, but not limited to, frequency compensation; control of, or alarms for, physical systems; or monitoring or measuring physical parameters of interest. The level of accuracy and repeatability attainable in a highly compact sensing module or device may be applicable to many medical applications monitoring or measuring physiological parameters throughout the human body including, not limited to, bone density, movement, viscosity, and pressure of various fluids, localized temperature, etc. with applications in the vascular, lymph, respiratory, digestive system, muscles, bones, and joints, other soft tissue areas, and interstitial fluids.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A propagation tuned oscillator (PTO) to maintain positive closed-loop feedback of energy waves in an energy propagating structure where energy waves propagate through a medium configured to couple to the muscular-skeletal system such that detection of a propagated energy wave initiates an energy wave emission into the medium, where the medium is configured to measure a parameter of the muscular-skeletal system, and where the parameter affects the medium.

2. The PTO of claim 1 where the propagation tuned oscillator tunes a resonant frequency of the energy waves in accordance with physical changes in the energy propagating structure.

3. The PTO of claim 2 where an integer number of energy waves propagates in the medium when positive closed-loop feedback is applied.

4. The PTO of claim 2 where the PTO measures one of transit time, frequency, or phase of a propagated energy wave.

5. The PTO of claim 4 where a parameter to be measured is applied to the medium and where changes in the parameter affect one of transit time, frequency, or phase of a propagated energy wave.

6. The PTO of claim 4 where a positive closed-loop feedback path of the PTO comprises a transducer driver configured to drive at least one transducer for the emission of energy waves into the medium, the energy propagating structure, and a zero-crossing receiver configured to detect the propagated energy wave.

7. The PTO of claim 4 where the positive closed-loop feedback path of the PTO comprises a transducer driver configured to drive at least one transducer for the emission of energy waves into the medium, the energy propagating structure, and a edge-detect receiver configured to detect the propagated energy wave.

8. The PTO of claim 4 where the energy propagating structure comprises:
a first transducer;
the medium where the first transducer is coupled to the medium at a first location; and
a second transducer coupled to a second location of the medium.

9. The PTO of claim 8 where a series and parallel resonance of the first transducer is configured not to overlap a series and parallel resonance of the second transducer.

10. The PTO of claim 4 where the energy propagating structure comprises:
a transducer;
the medium where the transducer is coupled to the medium at a first location; and
a reflecting surface at a second location of the medium.

11. A wireless sensing assembly comprising:
a sensor comprising:
a first transducer;
a medium where the first transducer is coupled to the medium at a first location; and
a second transducer where the second transducer is coupled to a second location of the medium and where a series and parallel resonance of the first transducer does not overlap a series and parallel resonance of the second transducer;
a propagation tuned oscillator operatively coupled to the sensor to maintain positive closed-loop feedback of energy waves in an energy propagating structure where energy waves propagate through a medium such that detection of a propagated energy wave initiates an energy wave emission into the medium and where the wireless sensing assembly comprises one or more load surfaces, an accelerometer, electronic circuitry, a transceiver, and an energy supply, to measure applied forces and transmit measurement data to a secondary system for further processing and display.

12. The wireless assembly of claim 11 where the medium is a waveguide.

13. The wireless assembly of claim 11 where the medium is compressible.

14. A method of measuring a parameter of the muscular-skeletal system comprising the steps of:
applying the parameter of the muscular-skeletal system to a medium;
maintaining positive closed-loop feedback to sustain the emission of energy waves in the medium;
measuring one of transit time, frequency, or phase of propagated energy waves; and
relating the transit time of one or more propagated energy waves to the parameter being measured.

15. The method of claim 14 further including the step of tuning a resonant frequency of energy waves in accordance with physical changes of the medium where a number of energy waves in the medium is an integer number.

16. The method of claim 14 further including the steps of:
detecting wave fronts of propagated energy waves; and
emitting an energy wave into the medium upon detecting a wave front.

17. The method of claim 14 further including the steps of:
detecting zero crossings of propagated energy waves; and
emitting an energy wave into the medium upon detecting a zero-crossing.

18. The method of claim 14 further including a step of propagating energy waves through a compressible waveguide.

* * * * *